United States Patent [19]

Yaffe

[11] 4,281,014
[45] Jul. 28, 1981

[54] STABILIZED COMPOSITIONS CONTAINING N-AMINOSULFENYLATED DERIVATIVES OF CARBOFURAN

[75] Inventor: Jerome Yaffe, El Cerrito, Calif.
[73] Assignee: FMC Corporation, Philadelphia, Pa.
[21] Appl. No.: 156,290
[22] Filed: Jun. 4, 1980
[51] Int. Cl.³ ............... A01N 25/22; C07D 307/86; A01N 47/18
[52] U.S. Cl. .................... 424/285; 424/246; 424/250; 424/267; 424/274; 544/58.7; 544/376; 546/196; 260/326.34; 260/346.73
[58] Field of Search ............ 424/246, 267, 250, 274, 424/285; 544/58.7, 376; 546/196; 260/326.34, 346.73

[56] References Cited

U.S. PATENT DOCUMENTS

| | | | |
|---|---|---|---|
| 3,867,526 | 2/1975 | Hennart et al. | 424/219 |
| 3,891,759 | 6/1975 | Aries | 424/219 |
| 3,952,102 | 4/1976 | Albrecht et al. | 424/276 |
| 4,006,231 | 2/1977 | Black et al. | 424/248.5 |

OTHER PUBLICATIONS

Chem. Absts. 77, 143818y (1972).
Chiu et al., Pestic. Biochem. Physicol., 5, p. 359, (1975).
"Thiodan ® Formulators Manual", Niagara Chem. Div. FMC Co., Middleport, N.Y. 14105, Sep. 1, 1971, pp. 1–4,7; Kronox-S data sheets.

*Primary Examiner*—Henry R. Jiles
*Assistant Examiner*—Bernard Dentz
*Attorney, Agent, or Firm*—Richard L. Hansen; Henry R. Ertelt

[57] ABSTRACT

Insecticidal compositions containing N-aminosulfenyl derivatives of carbofuran are stabilized against spontaneous decomposition by incorporating an epoxide compound therein.

9 Claims, No Drawings

STABILIZED COMPOSITIONS CONTAINING N-AMINOSULFENYLATED DERIVATIVES OF CARBOFURAN

BACKGROUND OF THE INVENTION

This invention relates to insecticidal compositions; more specifically, the stabilization of N-aminosulfenyl derivatives of carbofuran by adding an epoxide compound thereto.

U.S. 4,006,231 discloses insecticidal (methyl) (aminosulfenyl)carbamic acid esters of 2,3-dihydro-2,2-dimethyl-7-benzofuranol, as well as formulated insecticidal compositions containing such carbamates in admixture with a carrier. The common name for 2,3-dihydro-2,2-dimethyl-7-benzofuranyl methyl carbamate is carbofuran, and the N-aminosulfenyl derivatives of carbofuran are of commercial interest, because they exhibit lower mammalian toxicity than the parent carbofuran.

Investigation of the N-aminosulfenyl derivatives of carbofuran directed toward their commercialization has shown that both the technical grade derivatives and formulations thereof undergo decomposition, giving the materials an unacceptably short shelf life. It is known that one of the decomposition products is carbofuran. It has been reported that the N-S bond in N-sulfenylated derivatives of carbofuran is labile [Chiu, et al., *Pestic. Biochem. Physiol.,* 5, 359 (1975)].

It is fairly common that a pesticide exhibits a shorter than desired shelf life. Various antioxidants, inhibitors, and scavengers have been developed over the years for addition to pesticidal compositions to stabilize them against spontaneous decomposition. As a rule, different classes of compounds require different stabilizers, because the mechanisms of decomposition vary from one pesticide class to the next.

It is known in the art to stabilize organophosphate insecticides against decomposition by adding an epoxide compound to the formulated material [see, for example, U.S. Pat. No. 3,867,526]. Epoxide compounds are also known to stabilize formulations of the chlorinated hydrocarbon pesticide, endosulfan [see, for example, U.S. Pat. No. 3,952,102].

SUMMARY OF THE INVENTION

It is one object of this invention to provide stabilized insecticidal compositions containing N-aminosulfenyl derivatives of carbofuran. It is another object of this invention to provide a method by which both technical and formulated N-aminosulfenyl derivatives of carbofuran can be stabilized against spontaneous decomposition.

According to this invention there is provided a stabilized insecticidal composition comprising about 0.2 to 98% by weight insecticidal N-aminosulfenyl derivative of carbofuran and about 0.01 to 20% by weight epoxide compound.

Further, this invention provides a method to stabilize an insecticidal composition containing about 0.2 to 98% by weight insecticidal N-aminosulfenyl derivative of carbofuran which comprises incorporating therewith epoxide compound to constitute about 0.01 to 20% by weight of said composition.

The N-aminosulfenyl derivatives of carbofuran which are stabilized according to this invention have the formula 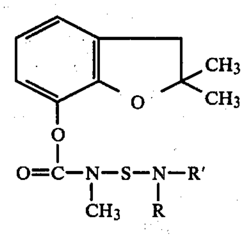 wherein R and and R′ may be the same or different, and each is alkyl of 1 to 8 carbon atoms which may contain an —O—, —S—, or —NR″— linkage (where R″ is lower (1 to 4 carbons) alkyl, benzyl, or phenyl), cycloalkyl of 3 to 6 carbon atoms, or benzyl, or R and R′ taken together with the nitrogen form a heterocyclic ring of 5 to 8 members which may contain an —S—, or —NR″—, which heterocyclic ring may be substituted by one or more alkyl, aralkyl, aryl, or alkoxy groups.

Among the aforesaid compounds, the instant invention is advantageously employed to stabilize those compounds wherein R and R′ are alkyl groups, preferably the same alkyl group, or where R is alkyl and R′ is benzyl. For example, 2,3-dihydro-2,2-dimethyl-7-benzofuranyl [methyl]-[(di-n-propyl)aminosulfenyl], or [(di-n-butyl)aminosulfenyl]-[methyl], or [methyl] [(di-n-pentyl)aminosulfenyl], or [methyl] [(N-methyl) (N-phenylmethyl)aminosulfenyl] carbamate. Among these, 2,3-dihydro-2,2-dimethyl-7-benzofuranyl [(di-n-butyl-)aminosulfenyl] [methyl] carbamate is especially useful.

DETAILED DESCRIPTION

In stabilizing N-aminosulfenyl derivatives of carbofuran according to this invention it is necessary to incorporate epoxide compound therewith. Useful epoxide compounds are those having an oxirane oxygen content of about 4 to 25%, based on the ratio of oxirane oxygen to the compound's molecular weight, and include alkyloxiranes, such as butylene oxide and epichlorohydrin, for example; aryloxiranes, such as styrene oxide, for example; epoxyethers, such as glycidyl ethers, for example, octyl and decyl glycidyl ethers; epoxycyclanes, such as cyclohexane oxide and 3,4-epoxycyclohexylmethyl-3,4-epoxycyclohexanecarboxylate, for example; and epoxidized naturally-occurring unsaturated fatty acid esters found in or derived from animal and vegetable oils.

It is preferred, however, to employ epoxidized vegetable oils; that is, vegetable oils having a saponification value of about 170 to 200 (the saponification value is the quantity of potassium hydroxide in milligrams required to saponify one gram of oil) and an iodine number of about 80 to 200 (the iodine number is the quantity of iodine in milligrams which reacts with one gram of oil) epoxidized to an oxirane content of about 4 to 12%. Epoxidized soybean and linseed oils are the most preferred epoxide compounds.

The amount of epoxide compound contained in a stabilized insecticidal composition of this invention will depend upon whether the N-aminosulfenyl derivative of carbofuran is present as essentially pure technical grade chemical or whether it has been diluted by admixture with a carrier. Technical grade N-aminosulfenyl derivatives of carbofuran are preferably stabilized by incorporating epoxide compound therewith to constitute about 2 to 16% by weight of the resultant insecticidal composition; about 4% by weight is generally optimum. The amount of epoxide compound necessary to stabilize a formulated insecticidal composition containing a carrier will depend upon the type of formulation. Such formulations, e.g., granules of large particle size, powdery dusts, wettable powders, emulsifiable concentrates, and solutions are disclosed in general terms in U.S. Pat. No. 4,006,231, incorporated herein by reference.

Emulsifiable concentrate formulations according to this invention contain about 100-500 gm/liter insecticide and consist of the following by weight:
(a) 11-57% technical N-aminosulfenyl derivative of carbofuran previously stabilized with epoxide compound
(b) 2-10% epoxide compound
(c) 4-10% blend of anionic/nonionic emulsifiers
(d) 26-83% solvent The total amount of epoxide compound in the emulsifiable concentrate formulations is about 2 to 13%. Example 1 illustrates a specific emulsifiable concentrate formulation according to this invention.

EXAMPLE 1

Emulsifiable Concentrate

| Component | % wt/wt |
| --- | --- |
| 2,3-Dihydro-2,2-dimethyl-7-benzofuranyl [(di-n-butyl)aminosulfenyl] [methyl] carbamate - contains 4% epoxidized soybean oil | 24.30 |
| Epoxidized soybean oil - 6.8-7.0% oxirane | 4.00 |
| Arylalkylsulfonate and polyethoxylated arylalkyl ether emulsifiers | 8.00 |
| Hydrocarbon solvents | 63.70 |
| | 100.00 |

Wettable powder formulations according to this invention have the following composition by weight:
(a) 35-57% technical N-aminosulfenyl derivative of carbofuran previously stabilized with epoxide compound
(b) 2-8% epoxide compound
(c) 3-6% triethanolamine
(d) 2-5% emulsifier
(e) 1-4% wetting and dispersing agent
(f) 15-25% hydrated aluminum magnesium silicate
(g) 19-30% inorganic oxide powder The total amount of epoxide compound in the wettable powder formulations is about 3 to 11%. Example 2 is a specific wettable powder formulation according to this invention.

EXAMPLE 2

Wettable Powder

| Component | % wt/wt |
| --- | --- |
| 2,3-Dihydro-2,2-dimethyl-7-benzofuranyl [(di-n-butyl)aminosulfenyl] [methyl] carbamate - contains 4% epoxidized soybean oil | 37.10 |
| Epoxidized soybean oil - 6.8-7.0% oxirane | 2.00 |
| Triethanolamine | 6.00 |
| Blended nonionic oil-soluble emulsifier | 4.50 |
| Wetting and dispersing agent | 1.00 |
| Silicate mineral clay | 24.70 |
| Hydrous magnesium silicate | 24.70 |
| | 100.00 |

Impregnated granular formulations according to this invention have the following composition by weight:
(a) 5-17% technical N-aminosulfenyl derivative of carbofuran previously stabilized with epoxide compound
(b) 1-8% epoxide compound
(c) 4-8% diethylene glycol
(d) 1-2% alkylarylpolyethoxylated alcohol
(e) 76-89% silicate mineral clay The amount of epoxide compound in the impregnated granular formulations is about 1-9%. A specific impregnated granular formulation according to this invention is illustrated in Example 3.

EXAMPLE 3

Impregnated Granules

| Component | % wt/wt |
| --- | --- |
| 2,3-Dihydro-2,2-dimethyl-7-benzofuranyl [(di-n-butyl)aminosulfenyl] [methyl] carbamate - contains 4% epoxidized soybean oil | 16.83 |
| Epoxidized soybean oil - 6.8-7.0% oxirane | 2.00 |
| Diethylene glycol | 7.98 |
| Alkylarylpolyethoxylated alcohol | 1.00 |
| Silicate mineral clay | 72.19 |
| | 100.00 |

Coated granular formulations according to this invention have the following composition by weight:
(a) 2-20% N-aminosulfenyl derivative of carbofuran previously stabilized with epoxide compound
(b) 70-93% washed silica sand core
(c) 1-3% polyvinyl acetate core coating
(d) 0-3% silicate mineral clay
(e) 0-2.7% water The amount of epoxide compound in the coated granule formulations is about 0.04-1.6%. A specific coated granular formulation according to this invention is illustrated in Example 4.

EXAMPLE 4

Coated Granules

| Component | % wt/wt |
| --- | --- |
| 2,3-Dihydro-2,2-dimethyl-7-benzofuranyl [(di-n-butyl)aminosulfenyl] [methyl] carbamate - 50% active base, contains 4% epoxidized soybean oil | 10.00 |
| Silica sand (20-40 mesh) | 87.00 |
| 50-55% Polyvinyl acetate/H$_2$O emulsion | 1.30 |
| Water | 1.70 |
| | 100.00 |

The resulting formulation is air-dried to fix the polyvinyl acetate coating on the silica sand core.

Dust formulations according to this invention have the following composition by weight:
(a) 1-20% N-aminosulfenyl derivative of carbofuran previously stabilized with epoxide compound
(b) 80-99% inorganic oxide powder The amount of epoxide compound in the dust formulations is about 0.01-1.8%. A specific dust formulation according to this invention is illustrated in Example 5.

EXAMPLE 5

Dust

| Component | % wt/wt |
|---|---|
| 2,3-Dihydro-2,2-dimethyl-7-benzofuranyl [(di-n-butyl)aminosulfenyl] [methyl] carbamate - 50% active base, contains 5% epoxidized soybean oil | 4.04 |
| Silicate mineral clay | 95.96 |
| | 100.00 |

Base formulations of N-aminosulfenyl derivatives of carbofuran, e.g., those used in dust and granule formulations, have the following composition by weight:
(a) 25-57% technical N-aminosulfenyl derivative of carbofuran previously stabilized with about 2-16% epoxide compound
(b) 1-5% epoxide compound
(c) 31-59% silicate mineral clay
(d) 2-8% wetting and dispersing agent
(e) 1-3% diethylene glycol The amount of epoxide compound in the base formulations is about 2-8%.

Stabilization with epoxidized soybean oil of insecticidal compositions containing various N-aminosulfenyl derivatives of carbofuran is illustrated in Table I. Table II illustrates the stabilization of technical grade 2,3-dihydro-2,2-dimethyl-7-benzofuranyl [(di-n-butyl)aminosulfenyl] [methyl] carbamate with various epoxide compounds.

TABLE I

Stabilization of N-Aminosulfenyl Derivatives of Carbofuran with Epoxidized Soybean Oil (ESO)

| Insecticidal Composition | | | Percent Loss of Derivative | |
|---|---|---|---|---|
| N-Aminosulfenyl Derivative | Solvent wt/wt | ESO wt/wt | After 1 month at 50° C. | After 3 months at 50° C. |
| (Di-n-butyl)-aminosulfenyl | 75% xylene | — | 24.0 | — |
| | 73% xylene | 2% | 6.4 | — |
| (N-Methyl)-(N-phenylmethyl)-aminosulfenyl[a] | 70% xylene | — | 22.6 | 63.3 |
| | 69% xylene | 1% | 3.6 | 21.3 |
| | 68% xylene | 2% | 18.9 | 18.1 |
| (Di-n-propyl)-aminosulfenyl | 75% xylene | — | 3.2 | 13.8 |
| | 74% xylene | 1% | 1.0 | 7.0 |

[a]compositions contain 5% emulsifier (wt/wt).

TABLE II

Stabilization of the (Di-n-butyl)aminosulfenyl Derivative of Carbofuran with Various Epoxide Compounds

| Epoxide Compound and Amount (wt/wt) | Oxirane Oxygen Content in Epoxide Compound | Percent Loss of Derivative in Six Months | |
|---|---|---|---|
| | | at 25° C. | at 50° C. |
| None | — | 1.3 | 72.2 |
| 2% Epoxidized soybean oil | 6.8-7% | — | 32.8 |
| 4% Epoxidized soybean oil | 6.8-7% | — | 10.7[a] |
| 8% Epoxidized soybean oil | 6.8-7% | — | 0.0 |
| 16% Epoxidized soybean oil | 6.8-7% | — | 0.0 |
| 2% Epoxidized linseed oil | 7-8% | 0 | 5.8 |
| 4% Epoxidized linseed oil | 7-8% | 4.0 | 6.6 |
| 8% Epoxidized linseed oil | 7-8% | 0 | 2.7 |
| 10% Epoxidized linseed oil | 9.2% | 3.4 | 10.4 |
| 10% Epoxidized butyl linseed Oil | 7.75-8.00% | 1.6 | 10.4 |
| 2% Mixed $C_8$— and $C_{10}$—alkyl glycidyl ethers | 7.0% | 0 | 3.2 |
| 4% Mixed $C_8$— and $C_{10}$—alkyl glycidyl ethers | 7.0% | 1.6 | 3.4 |
| 8% Mixed $C_8$— and $C_{10}$—alkyl glycidyl ethers | 7.0% | 0.5 | 2.5 |
| 3% 3,4-Epoxycyclohexyl methyl-3,4-epoxycyclohexane carboxylate | 12.0% | 0.5 | 4.6 |
| 4% 3,4-Epoxycyclohexyl methyl-3,4-epoxycyclohexane carboxylate | 12.0% | 2.6 | 10.9 |
| 5% Diepoxy carbutilate | 11.4% | — | 9.2 |
| 4% Octyl epoxytallate | 4.8% | 0 | 1.9 |

[a]Average of 2 experiments

I claim:

1. A stabilized insecticidal composition comprising about 0.2 to 98% by weight insecticidal N-aminosulfenyl derivative of carbofuran of the formula

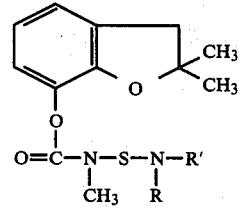

wherein R and R' may be the same or different, and each is alkyl of 1 to 8 carbon atoms which may contain an —O—, —S—, or —NR"— linkage (where R" is lower (1 to 4 carbons) alkyl, benzyl, or phenyl), cycloalkyl of 3 to 6 carbon atoms, or benzyl, or R and R' taken together with the nitrogen form a heterocyclic ring of 5 to 8 members which may contain an —S—, or —NR"—, which heterocyclic ring may be substituted by one or more alkyl, aralkyl, aryl, or alkoxy groups, and about 0.01 to 20% by weight epoxide compound.

2. A composition of claim 1 wherein the N-aminosulfenyl derivative of carbofuran is selected from those compounds wherein R and R' are alkyl or R is alkyl and R' is benzyl.

3. A composition of claim 2 wherein the N-aminosulfenyl derivative of carbofuran is selected from the (di-n-propyl)-, (di-n-butyl)-, (di-n-pentyl)-, or (N-methyl)-(N-phenylmethyl)aminosulfenyl derivative.

4. A composition of claim 3 wherein the N-aminosulfenyl derivative of carbofuran is 2,3-dihydro-2,2-dimethyl-7-benzofuranyl [(di-n-butyl)aminosulfenyl]-[methyl] carbamate.

5. A composition of claim 1 wherein the epoxide compound has an oxirane oxygen content of about 4 to 25% and is selected from alkyloxiranes, aryloxiranes, epoxyethers, epoxycyclanes, and epoxidized naturally-occurring unsaturated fatty acid esters found in or derived from animal and vegetable oils.

6. A composition of claim 5 wherein the epoxide compound is an epoxidized vegetable oil.

7. A composition of claim 6 wherein the vegetable oil is soybean oil or linseed oil.

8. A composition of claim 4 or 6 wherein the epoxide compound is epoxidized soybean oil.

9. A method to stabilize an insecticidal composition containing about 0.2 to 98% by weight insecticidal N-aminosulfenyl derivative of carbofuran of the formula $$\begin{array}{c} \text{[benzofuran ring with } \text{CH}_3, \text{CH}_3, \text{O}\text{]} \\ \text{O} \\ \text{O=C-N-S-N-R'} \\ \quad\quad\;\; | \quad\;\; | \\ \quad\quad\;\; \text{CH}_3 \;\; \text{R} \end{array}$$

wherein R and R' may be the same or different, and each is alkyl of 1 to 8 carbon atoms which may contain an —O—, —S—, or —NR"— linkage (where R" is lower (1 to 4 carbons) alkyl, benzyl, or phenyl), cycloalkyl of 3 to 6 carbon atoms, or benzyl, or R and R' taken together with the nitrogen form a heterocyclic ring of 5 to 8 members which may contain an —S—, or —NR"—, which heterocyclic ring may be substituted by one or more alkyl, aralkyl, aryl, or alkoxy groups, which comprises incorporating therewith epoxide compound to constitute about 0.01 to 20% by weight of said composition.

* * * * *